(12) United States Patent
Nonomura

(10) Patent No.: US 9,828,299 B2
(45) Date of Patent: Nov. 28, 2017

(54) METHODS FOR RENDERING MICELLAR COORDINATION COMPLEXES SAFE FOR THE TREATMENT OF PLANTS AND FORMULATIONS FOR SAME

(71) Applicant: Innovation Hammer LLC, Powell, OH (US)

(72) Inventor: Arthur M. Nonomura, Litchfield Park, AZ (US)

(73) Assignee: Innovation Hammer, LLC, Powell, OH (US)

( * ) Notice: Subject to any disclaimer, the term of this patent is extended or adjusted under 35 U.S.C. 154(b) by 0 days.

(21) Appl. No.: 14/397,718

(22) PCT Filed: Mar. 7, 2013

(86) PCT No.: PCT/US2013/029535
§ 371 (c)(1),
(2) Date: Oct. 29, 2014

(87) PCT Pub. No.: WO2013/176731
PCT Pub. Date: Nov. 28, 2013

(65) Prior Publication Data
US 2015/0133298 A1 May 14, 2015

Related U.S. Application Data

(60) Provisional application No. 61/649,422, filed on May 21, 2012.

(51) Int. Cl.
| | |
|---|---|
| *C05D 9/02* | (2006.01) |
| *A01N 37/42* | (2006.01) |
| *A01N 55/02* | (2006.01) |
| *A01N 59/06* | (2006.01) |
| *A01N 59/16* | (2006.01) |
| *A01N 59/20* | (2006.01) |

(52) U.S. Cl.
CPC ............... *C05D 9/02* (2013.01); *A01N 37/42* (2013.01); *A01N 55/02* (2013.01)

(58) Field of Classification Search
None
See application file for complete search history.

(56) References Cited

U.S. PATENT DOCUMENTS

| | | |
|---|---|---|
| 3,245,776 A | 4/1966 | Rubin |
| 3,578,619 A | 5/1971 | Reeder |
| 4,111,678 A | 9/1978 | Downer |
| 4,264,478 A | 4/1981 | Seldner |
| 4,338,432 A | 7/1982 | Lawson et al. |
| H000224 H | 3/1987 | Malik et al. |
| H000303 H | 7/1987 | Malik et al. |
| 5,241,781 A | 9/1993 | Malczyk |
| 5,413,928 A | 5/1995 | Weathers et al. |
| 5,458,837 A | 10/1995 | Roberts et al. |
| 5,549,718 A | 8/1996 | Lerouge et al. |
| 5,549,729 A | 8/1996 | Yamashita |
| 5,634,959 A | 6/1997 | Beaty |
| 5,688,981 A | 11/1997 | Nonomura |
| 5,767,378 A | 6/1998 | Bojsen et al. |
| 5,797,976 A | 8/1998 | Yamashita |
| 5,958,104 A | 9/1999 | Nonomura et al. |
| 5,962,717 A | 10/1999 | Nonomura et al. |
| 5,965,150 A | 10/1999 | Wada et al. |
| 5,993,504 A | 11/1999 | Nonomura et al. |
| 6,020,288 A | 2/2000 | Nonomura et al. |
| 6,092,302 A | 7/2000 | Berrigan |
| 6,110,867 A | 8/2000 | Glenn et al. |
| 6,258,749 B1 | 7/2001 | Nonomura |
| 6,309,440 B1 | 10/2001 | Yamashita |
| 6,318,023 B1 | 11/2001 | Yamashita |
| 6,358,293 B1 | 3/2002 | Nonomura |
| 6,407,040 B1 | 6/2002 | Nichols |
| 6,440,907 B1 | 8/2002 | Santora et al. |
| 6,451,739 B1 | 9/2002 | Kober et al. |
| 6,464,995 B1 | 10/2002 | Sekutowski et al. |
| 6,544,511 B2 | 4/2003 | Nishimura et al. |
| 6,699,977 B1 | 3/2004 | Gerrish et al. |
| 6,730,537 B2 | 5/2004 | Hutchison et al. |
| 6,746,988 B2 | 6/2004 | Hopkinson et al. |
| 6,826,866 B2 | 12/2004 | Moore et al. |
| 8,093,182 B2 | 1/2012 | Nonomura |

(Continued)

FOREIGN PATENT DOCUMENTS

| | | |
|---|---|---|
| EP | 0811858 A2 | 12/1997 |
| EP | 1306403 A1 | 5/2003 |

(Continued)

OTHER PUBLICATIONS

European communication dated Nov. 25, 2015 in corresponding European patent application No. 13794107.6.
Eurasian communication, with English translation, dated Dec. 15, 2015 in corresponding Eurasian patent application No. 201492180.
Australian communication dated Dec. 17, 2015 in corresponding Australian patent application No. 2013266917.
Kumar, "Synthesis Methods of Metal Chelates beta-ketoesters—(A Critical Review)", Oriental Journal of Chemistry, vol. 27, No. 1, p. 347-349, Dec. 31, 2011.

(Continued)

*Primary Examiner* — Tracy Vivlemore
*Assistant Examiner* — Monica A Shin
(74) *Attorney, Agent, or Firm* — Nields, Lemack & Frame, LLC

(57) ABSTRACT

Methods for rendering micellar coordination complexes for the treatment of plants, comprising the steps of mixing one or more ketoesters with other nutrients resulting in waterborne availability; applying a suitable volume of the resulting mixture to one or more plants; delivery to green plants; nutrimentally based growth of crops; and compositions for the same.

19 Claims, 3 Drawing Sheets

(56) References Cited

U.S. PATENT DOCUMENTS

| | | | |
|---|---|---|---|
| 8,937,054 B1 | 1/2015 | Martin | |
| 9,072,304 B2 | 7/2015 | Nonomura | |
| 9,277,697 B2 | 3/2016 | Nonomura | |
| 9,374,955 B2 | 6/2016 | Nonomura | |
| 2001/0003596 A1 | 6/2001 | Finnie et al. | |
| 2002/0177654 A1 | 11/2002 | Erdem et al. | |
| 2003/0128428 A1 | 7/2003 | Anderson | |
| 2005/0144670 A1 | 6/2005 | Fujiyama et al. | |
| 2005/0152146 A1 | 7/2005 | Owen et al. | |
| 2006/0142158 A1 | 6/2006 | Nonomura | |
| 2007/0056053 A1 | 3/2007 | Gray et al. | |
| 2008/0194407 A1 | 8/2008 | Ashmead et al. | |
| 2010/0081619 A1* | 4/2010 | Tedford | A01N 37/18 514/4.5 |
| 2011/0123803 A1 | 5/2011 | Yamanaka et al. | |
| 2011/0143941 A1* | 6/2011 | Archer | C03C 1/002 504/187 |
| 2011/0244011 A1 | 10/2011 | Jongedijk et al. | |
| 2012/0077679 A1 | 3/2012 | Nonomura | |
| 2014/0331555 A1* | 11/2014 | Nonomura | A01N 43/16 47/65.5 |
| 2015/0250117 A1 | 9/2015 | Nonomura | |
| 2015/0250171 A1 | 9/2015 | Nonomura | |
| 2015/0284299 A1 | 10/2015 | Coutant et al. | |
| 2017/0164562 A1 | 6/2017 | Nonomura | |

FOREIGN PATENT DOCUMENTS

| | | | | |
|---|---|---|---|---|
| ES | 2110894 A1 | 2/1998 | | |
| GB | 1268308 A | 3/1972 | | |
| JP | 2001-275498 A | 10/2001 | | |
| JP | 2003-517410 A | 5/2003 | | |
| JP | 2008-001550 A | 1/2008 | | |
| WO | WO 9325078 A1 * | 12/1993 | | A01C 1/06 |
| WO | 99/12868 A1 | 3/1999 | | |
| WO | 99/60093 A2 | 11/1999 | | |
| WO | 00/54568 A1 | 9/2000 | | |
| WO | 01/47360 A2 | 7/2001 | | |
| WO | 01/56384 A1 | 8/2001 | | |
| WO | 2009/135049 A1 | 11/2009 | | |

OTHER PUBLICATIONS

International Search Report and Written Opinion dated May 13, 2013 in corresponding PCT application No. PCT/US13/29535.
International Preliminary Report on Patentability dated Aug. 13, 2014 in corresponding PCT application No. PCT/US13/29535.
Canadian communication dated Sep. 15, 2016 in corresponding Canadian patent application No. 2,872,173.
Eurasian communication, with English translation, dated Aug. 22, 2016 in corresponding Eurasian patent application No. 201492180.
Australian communication dated Apr. 14, 2016 in corresponding Australian patent application No. 2013266917.
Eurasian communication, with English translation, dated Mar. 15, 2017 in corresponding Eurasian patent application No. 201492180/28.
European communication dated Dec. 13, 2012 in co-pending European patent application No. EP 05854833.
European communication dated Jun. 22, 2015 in co-pending European patent application No. 05854833.0.
International Search Report and Written Opinion dated Mar. 25, 2013 in co-pending PCT application No. PCT/US2012/065768.
International Preliminary Report on Patentability completed Oct. 14, 2013 in co-pending PCT application No. PCT/US12/65768.
European communication dated Sep. 16, 2015 in co-pending European patent application No. 12851712.5.
European communication dated Jan. 28, 2016 in co-pending European patent application No. 12851712.5.
Japanese communication, with English translation, dated Apr. 19, 2016 in co-pending Japanese patent application No. 2014-542541.
Australian communication dated Oct. 14, 2016 in co-pending Australian patent application No. 2012340849.
Japanese communication, with English translation, dated Dec. 6, 2016 in co-pending Japanese patent application No. 2014-542541.
Australian communication dated Mar. 14, 2017 in co-pending Australian patent application No. 2012340849.
Aubert, et al., Journal of Experimental Botany, vol. 55, No. 406, pp. 2179-2189, Oct. 2004, "Methyl-B-D-glucopyranoside in higher plants: accumulation and intracellular localization in *Geum montanum* L. leaves and in model systems studied by 13C nuclear magnetic resonance".
Bacic, et al., Australian Journal of Plant Physiology 8(5), 1981, pp. 475-495, Abstract, "Chemistry and Organization of Aleurone Cell Wall Components From Wheat and Barley".
Baradas, et al., Agronomy Journal, V. 68, Nov.-Dec. 1976, pp. 848-852, "Reflectant Induced Modification of Soybean Canopy Radiation Balance V. Longwave Radiation Balance".
Barratt, et al., Physiologia Plantarum 105: 207-217, 1999, "Metabolism of exogenous auxin by *Arabidopsis thaliana*: Identification of the conjugate N-(indol-3-ylacetyl)-glutamine and initiation of a mutant screen".
Benson, Annual Review of Plant Biology, 2002, 53:1-25, "Paving the Path".
Benson, Photosynthesis Research 73: 29-49, 2002, "Following the path of carbon in photosynthesis: a personal story".
Benson, et al., Journal of Plant Nutrition, 32: 1185-1200, 2009, "The Path of Carbon in Photosynthesis: XXV. Plant and Algal Growth Responses to Glycopyranosides".
Benson, et al., Photosynthesis Research: An International Journal, vol. 34, No. 1, Oct. 1992, 1 pg. Abstract, P-522, "The Path of Carbon in Photosynthesis: Methanol Inhibition of Glycolic Acid Accumulation".
Biel, et al., Journal of Plant Nutrition, 33: 902-913, 2010, "The Path of Carbon in Photosynthesis. XXVI. Uptake and Transport of Methylglucopyranoside Throughout Plants".
Brewer, et al., Proc. Nat. Acord. Sci, USA, vol. 70, No. 4, pp. 1007-1111, Apr. 1973, "Binding of 13C-Enriched a-Methyl-D-Glucopyranoside to Concanavalin A as Studied by Carbon Magnetic Resonance".
Calvin, et al., Science, New Series, vol. 107, No. 2784, May 7, 1948, pp. 476-480, "The Path of Carbon in Photosynthesis".
Calvin, Melvin Calvin Nobel Lecture, Dec. 11, 1961, pp. 618-644, "The path of carbon in photosynthesis".
Carpin, et al., Plant Cell, vol. 13, pp. 511-520, Mar. 2001, "Identification of a Ca2+-Pectate Binding Site on an Apoplastic Peroxidase".
Catoire, et al., Eur Biophys J (1998) 27: 127-136, "An efficient procedure for studying pectin structure which combines limited depolymerization and 13C NMR".
Cheng, et al., Department of Pharmacy, National University of Singapore, Taylor & Francis, vol. 30, No. 4, 2004, pp. 359-367, 1 pg. Abstract, "Insulin-Loaded Calcium Pectinate Nanoparticles: Effects of Pectin Molecular Weight and Formulation pH".
Comparot, et al., Journal of Experimental Botany, vol. 54, No. 382, pp. 595-604, Jan. 2003, "Function and specificity of 14-3-3 proteins in the regulation of carbohydrate and nitrogen metabolism".
Cortes, et al., Plant Physiology, Feb. 2003, vol. 131, pp. 824-837, "In Plants, 3-O-Methylglucose is Phosphorylated by Hexokinase But Not Perceived as a Sugar".
Decreux, et al., Plant and Cell Physiology, 2005, 46(2): 268-278, "Wall-associated Kinase WAK1 Interacts with Cell Wall Pectins in a Calcium-induced Conformation".
Easterwood, Fluid Journal, vol. 10, No. 36, Jan. 2002, 3 pages, XP055046731, "Calcium's Role in Plant Nutrition".
Fall, et al., Trends in Plant Science, Sep. 1996, vol. 1, No. 9, pp. 296-301, "Leaf methanol—the simplest natural product from plants".
Feagley, et al., Texas Agricultural Extension Service, Texas A & M University Digital Library, Publications, L-5212, Sep. 1998, pp. 1-4, XP055046729, "Using Soluble Calcium to Stimulate Plant Growth".
Ferguson, et al., PNAS, Jan. 9, 2007, vol. 104, No. 2, pp. 513-518, "Signal transduction pathway of TonB-dependent transporters".

(56) References Cited

OTHER PUBLICATIONS

Fishman, et al., Biomacro Molecules, 5(2), pp. 334-341, 1 pg. Abstract, Jan. 2004, "Nano Structure of Native Pectin Sugar Acid Gels Visualized by Atomic Force Microscopy".
Fishman, et al., J Agric Food Chem, Sep. 2001, 49(9): 4494-501, 1 pg. Abstract, "Solvent effects on the molecular properties of pectins".
Gerard, J. Phycol. 33, 800-810 (1997), "The Role of Nitrogen Nutrition in High-Temperature Tolerance of the Kelp, Laminaria saccharina (Chromophyta)".
Gibson, Plant Physiology, Dec. 2000, vol. 124, pp. 1532-1539, "Plant Sugar-Response Pathways. Part of a Complex Regulatory Web".
Goldenkova, et al., Russian Journal of Plant Physiology, vol. 49, No. 4, 2002, pp. 524-529, "The Expression of the Bacterial Gene for Xylose (Glucose) Isomerase in Transgenic Tobacco Plants Affects Plant Morphology and Phytohormonal Balance".
Goubet, et al., Plant Physiol. (1998) 116: 337-347, "Identification and Partial Characterization of the Pectin Methyltransferase 'Homogalacturonan-Methyltransferase' from Membranes of Tobacco Cell Suspensions".
Gout, et al., Plant Physiology, May 2000, vol. 123, pp. 287-296, "Metabolism of Methanol in Plant Cells. Carbon-13 Nuclear Magnetic Resonance Studies".
Griffiths, Royal Horticultural Society/Index of Garden Plants, 1992, 1994, 10 pages.
Guerrini, et al., Journal of Experimental Botany,1994, vol. 45, No. 9, pp. 1227-1233, "The effect of calcium chelators on microsomal pyridine nucleotide-linked dehydrogenases of sugarbeet cells".
Hoagland, et al., California Agricultural Experiment Station, Circular 347, Revised Jan. 1950, pp. 1-32, "The Water-Culture Method for Growing Plants Without Soil".
Hyatt, et al., Heterocycles, vol. 35, No. 1, 1993, pp. 227-234, "The Intermediacy of Sulfate Esters in Sulfuric Acid Catalyzed Acetylation of Carbohydrates".
Ichimura, et al., Annals of Botany 83: 551-557, 1999, "Possible roles of Methyl Glucoside and Myo-inositol in the Opening of Cut Rose Flowers".
Ichimura, et al., Biosci. Biotech. Biochem., 61(10): 1734-1735, 1997, "Identification of Methyl B-Glucopyranoside and Xylose as Soluble Sugar Constituents in Roses".
Jakubowska, et al., Journal of Experimental Botany, vol. 55, No. 398, pp. 791-801, Apr. 2004, "The auxin conjugate 1-0-indole-3-acetyl-B-D-glucose is synthesized in immature legume seeds by IAGlc synthase and may be used for modification of some high molecular weight compounds".
Josine et al., "Advances in Genetic Engineering for Plants Abiotic Stress Control;" African Journal of Biotechnology, vol. 10, No. 28, pp. 5402-5413, 2011.
Kaback, et al., PNAS, Jan. 9, 2007, vol. 104, No. 2, pp. 491-494, "Site-directed alkylation and the alternating access model for LacY".
Kamp, Hort Science 20(5): 879-881, 1985, "Control of Erysiphe cichoracearum on Zinnia elegans, with a Polymer-based Antitranspirant".
Lannoo, et al., Plant Cell Physiol. 2007, pp. 1-12, "The Jasmonate-Induced Expression of the nicotiana tabacum Leaf Lectin".
Goldenkova, et al., Russian Journal of Plant Physiology, vol. 49, No. 4, 2002, pp. 524-529, "The Expression of the Bacterial Gene for Xylose (Glucose) Isomerase in Transgenic Tobacco Plants Affects Plant Morphology and Jhytohormonal Balance".
Chimura, et al., Biosci. Biotech. Biochem., 61(10): 1734-1735, 1997, "Identification of Methyl B-Glucopyranoside and Xylose as Soluble Sugar Constituents in Roses".
Jakubowska, et al., Journal of Experimental Botany, vol. 55, No. 398, pp. 791-801, Apr. 2004, "The auxin mnjugate 1-0-indole-3-acetyl-B-D-glucose is synthesized in immature legume seeds by IAGlc synthase and may be ised for modification of some high molecular weight compounds".
Lasswell, et al., The Plant Cell, vol. 12, pp. 2395-2408, Dec. 2000, "Cloning and Characterization of IAR1, a Gene Required for Auxin Conjugate Sensitivity in Arabidopsis".
Leclere, et al., Plant Physiology, Jun. 2004, vol. 135, pp. 989-999, "IAR4, a Gene Required for Auxin Conjugate Sensitivity in Arabidopsis, Encodes a Pyruvate Dehydrogenase E1a Homolog".
Li, et al., Science, Oct. 7, 2005: 121-125, 1 pg. Abstract, "Arabidopsis H+-PPase a VP1 Regulates Auxin-Mediated Organ Development".
Markle, et al., Food and Feed Crops of the US, Jun. 1998, 2nd Edition, Revised, Descriptive List Classified According to Potentials for Pesticide Residues, 20 pages.
Miller, et al. Botanica Marina, vol. 45, 2002, pp. 1-8, "Evaluation of the Structure of the Polysaccharides from Chondria macrocarpa and Ceramium rubrum as Determined by 13C NMR Spectroscopy".
Moreshet, et al., Crop Science, vol. 19, Nov.-Dec. 1979, pp. 863-868, "Effect of Increasing Foliage Reflectance on Yield, Growth, and Physiological Behavior of a Dryland Cotton Crop".
Nonomura, et al., Advances in Photosynthesis—Fundamental Aspects, published Feb. 15, 2012, pp. 259-272, "The Path of Carbon in Photosynthesis—XVIII—Response of Plants to Polyalkylglucopyranose and Polyacylglucopyranose".
Nonomura, et al., Journal of Plant Nutrition, 34: 653-664, 2011, "The Path of Carbon in Photosynthesis. XXVII. Sugar-Conjugated Plant Growth Regulators Enhance General Productivity".
Nonomura, et al., Journal of Plant Nutrition, 35:12, pp. 1896-1909, 2012, "The Path of Carbon in Photosynthesis. XXIX. Glass Microbeads".
Nonomura, et al., Photosynthesis, 2013, Chapter 1, pp. 3-22, "The Path of Carbon in Photosynthesis, XXX, a-Mannosides", http://dx.doi.org/10.5772/55260, 22 pages.
Nonomura, et al., Proc. Natl. Acad. Sci., USA, vol. 89, pp. 9794-9798, Oct. 1992, "The path of carbon in photosynthesis: Improved crop yields with methanol".
Rao, Journal of Horticultural Science (1985), 60(1), pp. 89-92, "The effects of antitranspirants on leaf water status, stomatal resistance and yield in tomato".
Sheen, et al., Current Opinion in Plant Biology, 1999, 2: 410-418, "Sugars as signaling molecules".
Shen, et al., IEEE Transactions on Nanotechnology 4(5): 539-547, 1 pg. Abstract, 2005, "Synthesis and characterization of Ni-P-CNT's Nanocomposite Film for MEMS Applications".
Soundara, et al., Agric. Sci. Digest, 1981, 1(4): 205-206, "Effect of Antitranspirants and Reflectants on Pod Yield of Rainfed Groundnut".
Stanhill, et al., Agronomy Journal, V. 68, Mar.-Apr. 1976, pp. 329-332, "Effect of Increasing Foliage and Soil Reflectivity on the Yield and Water Use Efficiency of Grain Sorghum".
Stroud, PNAS, Jan. 30, 2007, vol. 104, No. 5, pp. 1445-1446, "Transmembrane transporters: An open and closed case".
Taylor, et al., Annals of Applied Biology, vol. 57, No. 2, Apr. 1966, pp. 301-309, XP055046581, "Studies on plant growth-regulating substances: XXI. The release of pectic substances from wheat coleoptile tissue incubated with solutions of ethylenediamin etetraacetic acid".
Woodward, et al., Annals of Botany 95: 707-735, 2005, "Auxin: Regulation, Action, and Interaction".
Thomas, et al., In Vitro Cellular & Developmental Biology—Plant, vol. 36, No. 6, Nov. 2000, pp. 537-542, XP055046711, "Effects of photo-oxidative loss of FeNa2Edta and of higher iron supply on chlorophyll content, growth and propagation rate in triploid watermelon cultures".
Trademark Electronic Search System, US Patent and Trademark Office, UPPLAUSE, serial No. 78889879, registered Mar. 13, 2007 to registrant Innovation Hammer LLC, pp. 1-2, data accessed Feb. 25, 2012.
Akzo Nobel Functional Chemicals, Micronutrients—healthy crops for healthy profits Brochure, "User Recommendation Sheet—Dissolvine E—Mg-6", Jun. 2002, pp. 1-2, XP055046728.
Wolf, et al., J. Phycol., vol. 21, pp. 388-396, 1985, "Growth and Branched Hydrocarbon Production in a Strain of Botryococcus braunii (Chlorophyta)".

(56) References Cited

OTHER PUBLICATIONS

Zbiec, et al., Electronic Journal of Polish Agricultural Universities, 2003, vol. 6, Issue 1, Series Agronomy, pp. 1-6, "Response of Some Cultivated Plants to Methanol As Compared to Supplemental Irrigation".

Zekaria-Oren, et al., Plant Disease/Mar. 1991, vol. 75, No. 3, pp. 231-234, "Effect of Film-Forming Compounds on the Development of Leaf Rust on Wheat Seedlings".

Ziv, et al., Plant Pathology (1987) 36, pp. 242-245, "The Effect of film-forming anti-transpirants on leaf rust and powdery mildew incidence on wheat".

Ziv et al. Plant Disease/May 1992, vol. 76, No. 5, pp. 513-517, "Effects of Bicarbonates and Film-Forming Polymers on Cucurbit Foliar Diseases".

Office action dated Jun. 29, 2016 in co-pending U.S. Appl. No. 14/359,455.

Office action dated Oct. 20, 2016 in co-pending U.S. Appl. No. 14/359,455.

Final rejection dated Mar. 27, 2017 in co-pending U.S. Appl. No. 14/359,455.

Leclere, et al., Plant Physiology, Jun. 2004, vol. 135, pp. 989-999, IAR4, a Gene Required for Auxin Conjugate Sensitivity in *Arabidopsis*, Encodes a Pyruvate Dehydrogenase E1a Homolog.

Ziv, et al., Plant Disease/May 1992, vol. 76, No. 5, pp. 513-517, "Effects of Bicarbonates and Film-Forming Polymers on Cucurbit Foliar Diseases".

Canadian communication dated May 25, 2017 in corresponding Canadian patent application No. 2,872,173.

European communication dated Apr. 26, 2017 in corresponding European patent application No. 13794107.6.

International Search Report and Written Opinion dated Sep. 5, 2017 in co-pending PCT application No. PCT/US2017/028489.

\* cited by examiner

FIG. 1

Schematic showing the flow of processes from left to right resulting in methods and compositions for the treatment of photosynthetic organisms with ketoesters. In the example of FIG.1, the input of ketoester is safened by admixture of N and P; a plant cell is exposed to the solution of ketoester and micelles are transepidermally transported into the cell; components are metabolized; (N into enzymes and P into ADP-ATP); and the path from these sources of exogenous C, N and P, leading to photosynthate.

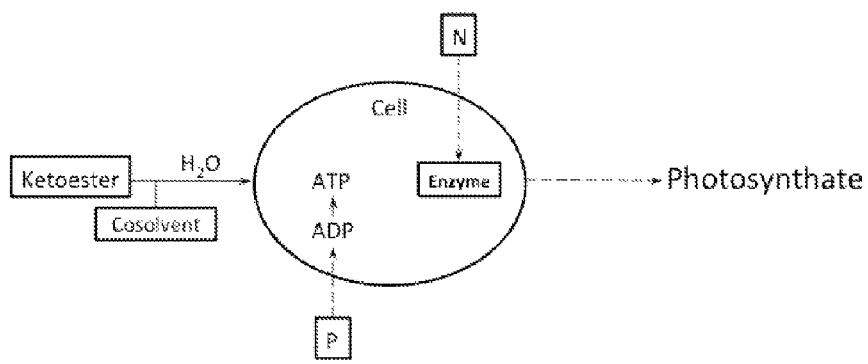

Schematic of methods and compositions for a micellar nanoparticle. The example of FIG. 2 shows the flow from top to bottom and left to right, wherein, a metal-ketoester is dissolved in a compatible ketoester. The composition is mixed into aqueous solution at the Critical Micelle Concentration of the ketoester resulting in the micellar nanoparticle.

FIG. 3

Representative samples from Control (left) and Treated (right) populations of Golden Barrel Cactus (*Echinocactus grusonii*) are exhibited in FIG. 3. The preferred exemplary formulation of Example 2 was applied as a foliar treatment while the control plants were given the same nutrients without the ketoester, glycoside and isopropanol. After 16 weeks, the diameters of the plants beneath spines were measured. The results showed that the nutrient controls averaged 10 cm mean diameter and the treated population averaged 12.5 cm mean diameter; statistically significant within 95% confidence interval; $p = 0.01$; $n = 10$.

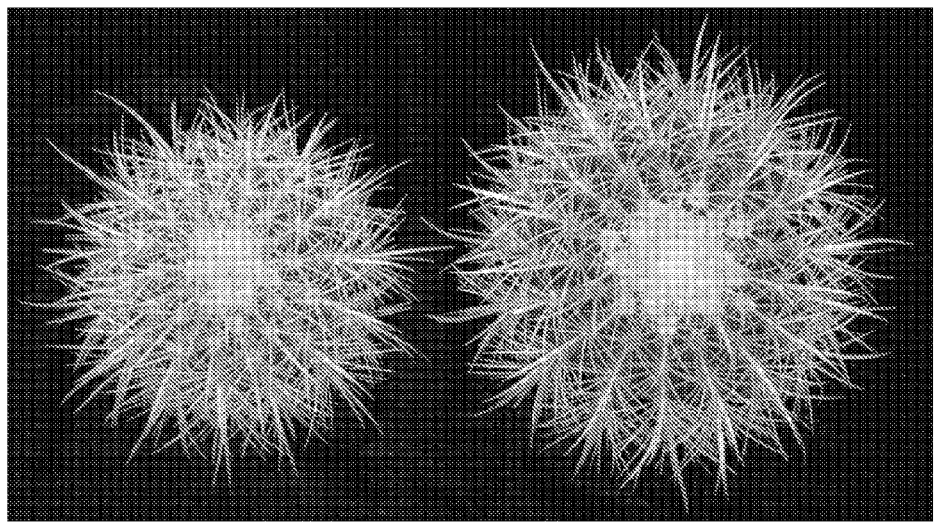

METHODS FOR RENDERING MICELLAR COORDINATION COMPLEXES SAFE FOR THE TREATMENT OF PLANTS AND FORMULATIONS FOR SAME

This application claims priority of provisional application Ser. No. 61/649,422 filed May 21, 2012, the disclosure of which is hereby incorporated by reference.

FIELD

The embodiments disclosed herein relate to methods and formulations for treating photosynthetic organisms, and more specifically, to methods for applying to flowering plants, formulations comprising one or more ketoesters; one or more micellar coordination complexes; and compositions of matter for delivery into such organisms, particularly agricultural crops.

BACKGROUND

The continued increase of the population of the world has maintained regions in jeopardy of famine while, at the same time, pollution driven shortages of drinking water occur at alarming rates; therefore, the simultaneous reduction of nutrient cycling from agricultural runoff and significant enhancement of photosynthetic yields are of necessary benefits to humanity. Indeed, when fertilizers are injected into the soil, there is only 50% nitrogen fertilizer efficiency and 10% phosphorus efficiency, and the remainder becomes pollution. Thus, a solution to the problem of groundwater contamination is to feed plants essential nutrients through foliage such that fertilizers are not injected into the ground and by application of efficiently metabolized fertilizers.

In accordance with the embodiments disclosed herein, foliar input of nutrients is enhanced by a synergistic metabolism of organic and mineral components of coordination complexes. The synergistic organic component of the embodiment is a ketoester and by formulation at relatively high concentrations, the entire complex is rendered to amphipathic micelles that effect phase transfer of nutrients into nonpolar organic compounds typical of cuticular waxes of foliage. In addition, certain ketoesters are of transmembrane domains assuring penetrative transport across membranes and into a plant cell; thereby, highly efficient uptake of valuable nutritive elements is realized by the embodiments, disclosed herein. It would be of benefit to agriculture to reduce ground contamination by optimizing the uptake of foliar nutrient applications through these novel systems, as well. Taken together, input of levels of nutritive elements that are sufficiently concentrated to sustain growth, that is, applying otherwise phytotoxic levels without negative effect, is realized by embodiments of micellar coordination complexes disclosed herein.

SUMMARY

The embodiments disclosed herein are the result of the discovery that at least critical micelle concentrations (CMC) of ketoesters may be made into compositions of which the compounds themselves serve as nutrient resources for photosynthetic organisms, including photosynthetic bacteria, algae, lichen, bryophytes, cryptophytes, and plants. As such, ketoesters may be appropriately formulated with agrochemicals and are rendered into aqueous compositions that are capable of facilitating the growth of photosynthetic organisms, particularly plants. The methods disclosed herein are applied to safely enhance the balanced metabolism of exogenous components that contribute to the productivity of photosynthetic organisms, while, at the same time, are coordination complexes; that, further, may be made to have the properties of micelles; and moreover, make micellar nanoparticulates in water. Thus, the embodiments first provide compositions of coordination complexes that function as fertilizers. Generally insoluble in water, ketoester coordination complexes are, for the most part, biphasic in water. These separated phases are inconvenient in agricultural fields and may pose insurmountable difficulties to the grower because water is the solute of choice. Additionally, with respect to the application of micronutrients as the mineral component of a coordination complex, the metabolic requirement for exceedingly low concentrations, typically in the microMolar range, permit these micronutrients to be water borne within the range of micellar concentrations of some corresponding ketoesters, especially acetoacetate esters that may be soluble up to a milliMolar range. Therefore, by dissolving the relatively insoluble coordination complex into a corresponding ketoester, it can then exhibit over a thousand times the availability to an organism. Furthermore, compositions in compatible ketoesters and/or polar organic cosolvents results in the embodiment of a micellar coordination complex. Moreover, as a consequence of mixing in water, the product forms a micellar nanoparticle (MNP) that is available to a photosynthetic organism; and in the event that treatment of photosynthetic organisms with standalone organic solvents would result in phytotoxicity, the embodiments provide methods for safening.

Although the present inventor is not to be bound by any theory, the micellar nanoparticles of the embodiments disclosed herein are amphipathic; they are nonpolar outside and polar inside. When the MNP contacts a leaf of a plant, for example, the nonpolar exterior is attracted to the waxy cuticle that protects the outer surface of the leaf. Waxes are nonpolar and the waxy cuticle repels water so that the leaf maintains structural integrity in wet environments. The cargo of the MNP commits to a phase transfer into the wax. The wax acts like a time-release fertilizer capsule, allowing for the nutrients to be delivered and metabolized slowly over the longer duration. The greatest benefit is that the transmembrane transporter (symporter) itself is consumed as an energy-packed nutrient.

Therefore, the embodiments provide methods for the formulation of ketoesters, preferably, β-ketoesters, more preferably acetoacetate esters, and most preferably EAA; and in the case of root exposure, at preferably 0.1 to 1 mole percent (mol %); and for foliar applications, most preferably applied to plants at the critical micelle concentration (CMC) approximating 2 to 10 mol % and in the range up to solubility in water of approximately 3 to 8 mol %; and applying these compositions to photosynthetic organisms, preferably plants, to enhance growth.

It is therefore an object of the embodiments disclosed herein to provide a method for formulating a composition comprising one or more ketoesters, preferably acetoacetate esters, and applying the formulation to plants in a manner which enhances plant growth without compromising the plant.

It is a further object to provide a system for plant nutriment and growth, comprising metals and ketoesters rendered to micelles.

It is a further object to provide a system for treatment of photosynthetic organisms, particularly plants, and growth formulations for plants comprising ketoesters rendered as micelles, that are available and penetrative consistent with facilitation of transcuticular, transepidermal and transmembrane transport.

It is a further object to provide a plant treatment and growth formulation comprising ketoesters in a micellar system for one or more nutrimental compounds of photosynthetic organisms, particularly plants.

It is another object to provide micellar compositions of matter.

It is another object to provide a micellar ketoester-metal-ketoester as an MNP.

It is another object to provide micellar coordination complexes with one or more of another metabolizable cosolvent selected to decrease the CMC.

It is another object to provide safening by supplementation with one or more fertilizers; and to provide a treatment for photosynthetic organisms and growth, comprising ketoesters with enhanced micellar coordination complexes. For convenient utilization in the field, it would be of benefit to render ketoesters convenient to apply to photosynthetic organisms and readily safe for photosynthetic organisms by formulation in a cosolvent compatible with ketoesters and aqueous media and safened by admixture with nitrogen and phosphorus fertilizers.

It is a further object to provide a treatment and growth formulation for photosynthetic organisms comprising ketoesters as synergists to one or more glycosides.

It is yet another object to provide a ketoester-safened environment in the presence of glass microbeads to photosynthetic organisms under cultivation in saturated light intensity conditions conducive of photorespiration.

BRIEF DESCRIPTION OF THE DRAWINGS

FIG. 1 is a schematic representation of the flow of processes from left to right resulting in methods and compositions for the treatment of photosynthetic organisms with ketoesters, in accordance with certain embodiments;

FIG. 3 is a photograph of representative samples from Control (left) and Treated (right) populations of Golden Barrel Cactus (*Echinocactus grusonii*), in accordance with certain embodiments.

DETAILED DESCRIPTION

Figure 2:
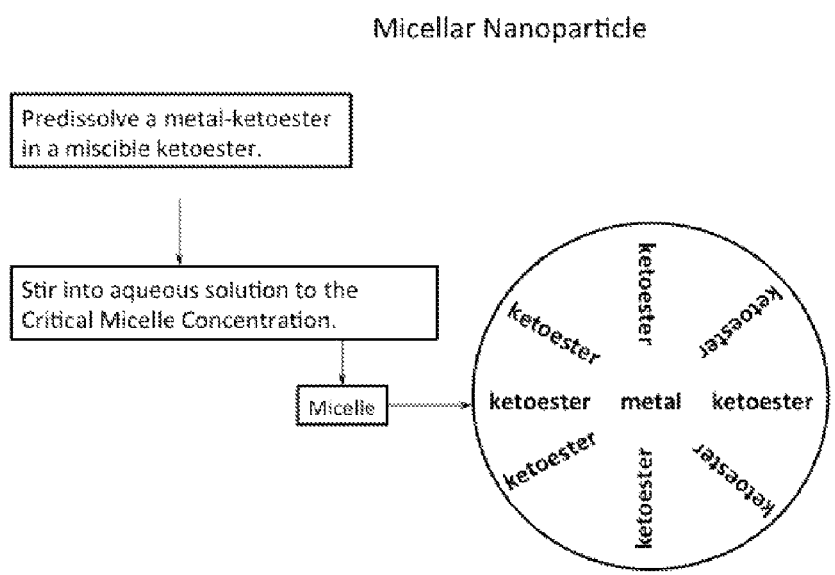
FIG. 2 is a schematic representation showing the flow from top to bottom and left to right, wherein, a metal-ketoester is dissolved in a compatible ketoester, in accordance with certain embodiments.

Embodiments disclosed herein formulate ketoesters into compositions of available fertilizers. Previously, concentrations of ketoesters have shown biphasic stability and, therefore, stood generally unavailable to plants; and although direct application of ketoesters to plants is possible, it is not worthwhile for lack of beneficial effect. However, ketoesters may be appropriately formulated with agrochemicals and rendered into micellar compositions; and in the embodiments disclosed herein, facilitate the growth of a photosynthetic organism as well as provide an array of beneficial nutrients. The methods disclosed herein make ketoesters readily available for uptake by photosynthetic organisms according to methods that balance metabolism of these exogenous components by production of coordination complexes and by applying them in micelles. Thus, embodiments disclose relatively insoluble compositions of coordination complexes; but with respect to the application of micronutrients, typically expressed in parts per million (ppm) concentrations, availability is achieved within an improved range of CMC. This is embodied in a micellar coordination complex, now solubilized in the range of percent (%) concentration. Therefore, by combining an insoluble coordination complex into a more highly soluble cosolvent, the resultant micelle may exhibit over a thousand times the effectiveness of the application. In summary, in certain embodiments methods are provided for enhancing the CMC and mixture into water by agitation to form micellar nanoparticles (MNPs). Thus, embodiments provide compositions of the resultant MNP.

A novel suitable synthesis from a micronutrient-salt to make the ketoester coordination complex, is as follows: Coordination complexes of micronutrients such as iron-EAA, zinc-EAA and copper-EAA may be manufactured or obtained commercially; whilst preferred divalent and trivalent nutrient metals include potassium, iron, manganese, zinc, and copper; and general complexation of an exemplary embodiment involves the following steps: Obtain a saturated solution by dissolving 1-1000 mg of soluble salts of the micronutrients, such as a metal-nitrate, -chloride, -salicylate, and/or -sulfate in 0.1-10 grams of water with stirring for 1 to 60 minutes or until the crystals are completely dissolved. All processes are undertaken within the range of 25°-50° C. Mix the aqueous solution with an equal or greater volume of ketoester or ketoesters, such as methyl-, ethyl-, propyl-, butyl-acetoacetate, and the like, with rapid agitation for 0.3 to 3 hours. When the cation is completely dissolved in the ketoester, it may sometimes be visibly displayed, such as by iron ions turning from brown to burgundy of a ketoester iron coordination complex. Mixing is stopped, allowing the return to biphasic solution with no agitation for 2-48 hours or more. The coordination complex may be collected in the ketoester-phase.

Ketoesters also are a source of metabolizable micellar nanoparticles for transepidermal transport; i.e., at or above the CMC of a ketoester. For example, when applied to a leaf at or above the CMC 6.48 mol % of the β-ketoester, EAA is an effective wetter and spreader of water-based solutions. This is particularly true of EAA when applied at CMC on leaves of green plants. Furthermore, by bringing the ketoester to CMC, other compounds in solution synergistically rise to CMC. For example, in the embodiments disclosed herein, physical characteristics of the CMC of the ketoester, MAA, are applied to create zinc depots.

Ketoesters may prove difficult to mix with water in the field, therefore, a convenient embodiment for synergistic enhancement of micelles in water is provided, herein. For example, 75 milliMolar (mM) EAA may be formulated with small amounts of cosolvent, for example, 10 mM n-butanol, to decrease the CMC. Ketoesters such as MAA and EAA may be formulated to varying degrees in a number of organic solvents that can decrease the CMC such as butanol, pentanol, and hexanol. In the preferred embodiment, it would be beneficial and highly practical to combine the properties of both compounds to decrease the CMC, as needed. Under particular circumstances where hydration is required, formulating with the shorter-chained alcohols, such as ethanol, is concomitant with increasing the CMC. Therefore, a cosolvent may comprise approximately equal quantities of a polar organic solvent, selected from $C_1$ to $C_7$ alcohols, such as, pentanol; acetonitrile; ketones, such as acetone; and combinations, thereof. The preferred formulation generally comprises an aliphatic alcohol such as in the following example: One or more ketoesters; such as, for example, methyl acetoacetate (MAA), propyl acetoacetate (PAA), and most preferably EAA, at a concentration of between about 0.1% to 5%. More specifically, for foliar applications, the ketoester is preferably at or above its CMC, for EAA preferably between about 0.3% to 3%, and further comprises predissolution in a cosolvent, preferably isopropanol and most preferably butanol at a concentration approximately from 0.01% to 10% to said concentration of said ketoester; and for root applications, the ketoester and cosolvent are premixed prior to addition to water at a reduced final aqueous concentration between about 0.001% to 0.3%. The lower rate for roots is intended to avoid lysis of bare root hairs.

The method may also comprise the step of adding one or more surfactants, such as a polyoxyethylene, polyoxypropylene, or a preferred random block copolymer, such as a BASF Pluronic, to the mixture, as well as fertilizers. The fertilizers may include a selection or mixtures of primary, secondary and micronutrients.

One suitable coordination complex may be made, for example, by dissolving 10 mg ferric nitrate nonahydrate, in 1 ml water with stirring at room temperature until the solution is clear with all crystals dissolved; to the aqueous iron solution, 1 ml MAA is added with rapid stirring for 5-50 minutes or more to allow formation of the coordination complex. The resulting Fe(III)-MAA is collected and further mixed with cosolvent, 9 g MAA. By thoroughly stirring into 1 L water, 1 to 10 ppm Fe is made available as micellar MAA-iron-MAA, hereinafter referred to as iron-MNP. This novel composition of iron-MNP may serve as a plant micronutrient to supplement deficiencies in a photosynthetic organism. The coordination complex is insoluble in water, but it is soluble in PAA, EAA and cosolvents. Other compositions include the following: micellar ketoester-zinc-ketoester, Zn-MNP; and micellar ketoester-copper-ketoester, Cu-MNP. In a similar manner, a ketoester-hexose may supplement other ketoesters to further create aqueous MNPs upon admixture to the CMC of the ketoester.

Inasmuch as application of large volumes of organic solvents to photosynthetic organisms may be phytotoxic, certain embodiments provide methods for rendering them safe. Certain readily assimilable cosolvents, for example, from $C_1$ to $C_7$ lower aliphatic alcohols such as propanol; and $C_5$ to $C_7$ ketoesters, such as, PAA; at concentrations in between 0.08-80% of the total volume may be safened for metabolism by plants. Inasmuch as the methods and formulations are designed to treat plants for the enhancement of growth, formulations of a coordination complex with safeners is followed by applying the mixture in a dry or liquid form directly to plants and/or by application to support media to reach roots. Specifically, the formulations make the carbon sources available in a manner that synergistically enables plants to metabolize CMC ketoesters by formulation with available nitrogen and phosphorus. Certain ketoesters such as acetoacetate-esters are substrates for specific proteins, for example in this case, acetoacetate CoA ligase. These enzymes require a source of nitrogen to build amino acids that contribute to their proteinaceous structures; furthermore, metabolism of ketoesters requires transfer of energy from compounds such as ATP and NADP, comprising phosphate. Therefore, safe treatment generally comprises the following: Preferably formulation with one or more sources of available nitrogen; most preferably supplementation with sources of nitrogen (N) and sources of available phosphorus (P); and most preferably with one or more β-ketoesters. The preferable mixture comprises low biuret urea nitrogen at a concentration between about 200 to 2000 ppm N and the most preferable mixture comprises a source of N with a source of P at a concentration between about 10 to 1000 ppm P; and then applying a suitable volume, within a range of 0.1 to 10 cc/1000 $cm^2$ plant, of the resulting mixture to one or more plants. The most preferable concentration of β-ketoesters is between about 0.1 to 2% generally, and preferably 0.01 to 1% for root application and 0.1 to 10% for shoot application. The preferred nitrogen sources comprise one or more of ammoniacal nitrogen and nitrate nitrogen, and the most highly preferred nitrogen sources are alcohol-soluble hexamine nitrogen and urea nitrogen; the preferred phosphorus sources are phosphate salts, e.g. potassium phosphates, sodium phosphates, ammonium phosphates, pyrophosphates, and the like. Generally, ketoesters exhibit low solubility transport into cellular penetration, the nutrimental synergism resulting in highly efficient dosage of agrochemicals. For example, N and P safeners in the preferred formulation comprise most preferably, ammonium phosphates between about 20 to 2000 ppm. The balanced input of a concentrated source of carbon for a plant eliminates lower limits of conventional phytotoxicity of approximately 250-500 ppm N and, in fact, permits foliar N up to 2000 ppm. The additional benefit of this synergism of safeners is an increased cycling duration between applications that may translate to savings for the grower.

Another preferred method for rendering high concentrations of ketoester safe for plant growth comprises the steps of: mixing one or more additional nutrients with safened formulations, resulting in a mixture comprising CMC ketoester; 200 to 2000 ppm nitrogen and 50 to 500 ppm phosphorus. Preferred primary fertilizers include available nitrogen, phosphorus, and potassium, abbreviated, N—P—K. Preferred secondary nutrients include available magnesium, calcium, and sulfur. Preferred micronutrients include iron, manganese, zinc, and copper. Preferred nutrients are not selected to the exclusion of other elements, ions, or salt, and depending on the situation, may be available in the soil and water in particular abundance such that supplementation is unnecessary for productivity. Suitable sources include salts and minerals generally known to the art, for example, the following: Primary fertilizers such as nitrates, nitrites, manures, ammoniacals, phosphates, pyrophosphates, phosphides, phosphites, potassium salts, potassium complexes, potassium ions, mixes, and the like; Secondary fertilizers such as Epsom salts, calcium salts, calcium carbonates, calcium nitrate, lime, sodalime, sulfates, ammonium sulfates, potassium sulfates, gypsum, mixes, and the like; and Micronutrients such as trace metals; coordination complexes; non-metallic borates, boric acid; metals of the elements, iron, zinc, manganese, copper, cobalt, nickel, silicon, and molybdenum; minerals; crystals; iron filings; ions; salts; mixes; and the like. Preferred organic salts of micronutrients include those of ketoesters such as Cu-EAA and Zn-EAA, and others as described herein; fatty acids such as Mn-oleate and Cu-oleate; and salicylates such as K-, Mn-, Zn-, and/or Cu-salicylate. For example, the most highly preferred micronutrient selection to the compositions of ketoesters may include 1 to 24 ppm iron as Fe-EAA; and applying a suitable amount of the resulting mixture to one or more plants. Soluble sources of micronutrients include hydrates, for example, $FeCl_2 \cdot 4H_2O$ and/or $Fe(NO_3)_3 \cdot 7H_2O$ are preferred. Moreover, where iron-deficiency of plants is diagnosed in a crop, supplementation with both iron and manganese is recommended and with Fe-EAA and Mn-EAA preferred. Furthermore, N may include preferably one or more of the following sources: ammoniacal N, such as ammonium sulfate; urea N such as methylene urea, urea, and preferably low biuret urea; amine/amide/amino N, such as alanine, arginine, asparagine, aspartic, cysteine, glutamic, glutamine, glycine, ornithine, proline, selenocysteine, taurine, tyrosine, histidine, isoleucine, leucine, lysine, methionine, phenylalanine, threonine, tryptophan, valine; salts; derivatives; and the like; and mixtures of amino acids; protein, such as, gluten, casein; hexamine N, such as Triazone®; and nitrate N, such as potassium nitrate, calcium nitrate, ammonium nitrate, sodium nitrate, and the like; and combinations, thereof. The amounts of plant nutrients are applied in accordance with fertilizer labeling of guaranteed analysis by governance boards, and are applied at rates known to the art. The safened formulations of ketoesters may be optimal under photorepiratory conditions; in particular, when for example, plants are cultivated in the presence of glass microbeads that refract light up to the phylloplane, will be beneficial to yields. Input of ketoester is safened by admixture of N and P In the example of FIG. 1; wherein, a plant cell is exposed to the solution of ketoester and micelles are transepidermally transported into the cell; components are metabolized; (N into enzymes and P into ADP-ATP); and the path from these sources of exogenous C, N and P, lead to photosynthate in a photosynthetic organism.

In certain embodiments, the safened mixture may be applied directly to the plant roots through the rooting medium and/or a foliar formulation may be applied to the foliage and all structures of the shoot. In formulations wherein the ketoester is at a concentration equal to or greater than the critical micelle concentration and the formulation is to be applied to plant foliage, the formulation of ketoester may function as an emulsifier, wetting agent, penetrant, surface active agent, micellar carbon, coordination complex, and MNP. Therefore, in certain embodiments its use preferably further comprises transporting into a plant, its tissues, and cells, combinations of essential nutrients known to the art at appropriate concentrations.

The safened formulation of ketoesters also may comprise 0.008% to 50% glycoside, wherein the ketoester is mixed with at least one or more glycoside in equimolar quantities in the presence of safeners and soluble trace metals as micronutrients. The resulting mixture may be applied to rooting media and then watered in or may be diluted first in an aqueous carrier and then applied to the media. A glycoside in the formulation is preferably at an equiMolar concentration to the ketoester or less, for example, 3 mM methyl-α-D-mannopyranoside with 68 mM EAA.

In certain embodiments the formulation may more specifically and preferably comprise one or more of the following: a β-ketoester, preferably EAA; one or more substituted sugars, preferably comprising one or more glycosides, preferably α-glycosides; most preferably a soluble glycoside, for example indoxylglycoside or alkylglycoside; one or more cosolvents, preferably one that decreases the CMC of the ketoester, such as butanol, in between the concentrations equal to the ketoester and greater, preferably between 0.003-10%; and presolubilized with a ketoester, preferably EAA; one or more aqueous carriers; one or more nutrient sources, preferably at least N, in between the range of 500-1500 ppm and P in the range of 100-500 ppm and micronutrients in the range of 0.0001-12 ppm; and, one or more surfactants.

In certain embodiments essential elements of nutrients include the following: Major nutrients, N, P, K; Secondary nutrients, Ca, S, Mg; and Micronutrients, Fe, Mn, Zn, B, Cu, Cl, Ni, Mo, Co and Si. Additionally, the formulations herein are useful when tank-mixed with various plant treatments. Green plant treatments include applications of active agents and active components to a plant or a part of a plant simultaneously or in serial sequence. For example, plant treatments include pesticides, insecticides, herbicides, biostimulants, antagonists, adjuvants, additives, synergists, systemic compounds, surfactants, spreaders, vitamins, minerals, salts, solvents, genetics, bioagents, and the like. Examples include the following: pesticides such as plant growth regulator, insecticide, herbicide, and the like; systemics such as insecticide, acetamiprid, and the like; vitamins such as vitamin B, and the like; minerals such as limestone, iron, sulfur, manganese, epsom salt, calcium, and the like; salts such as ammonium nitrate, ammonium sulfate, potassium permanganate, potassium phosphate, calcium nitrate, and the like; cosolvents such as acetone, pentanol, propanol, lipids, water, and the like; genetics such as genes, sequences, RNA, DNA, plasmids, genomes, and the like; bioagents such as microbial, yeast, bacteria, virus, vectors, and the like; and colorants, dyes, and pigments such as methylene dyes, cobalt blue and indigo.

When applying to the foliage, the formulation may further comprise one or more aqueous surfactants, such as about 0.02 to 1% random block copolymer, e.g., Pluronic L-62 (BASF), and applying the resulting mixture by spraying, misting or electrostatics to the plant foliage in an amount between about 1 to 100 gallons per acre, preferably 20 to 80 gallons per acre.

The methods and formulations may be advantageously used with any type of plant or plant-like organisms which synthesize cellulose, including, but not limited to, plants with stems, roots and leaves and plant-like organisms such as protistans, yeasts, fungi, molds and algae.

Unless otherwise defined, all technical and scientific terms employed herein have their conventional meaning in the art. As used herein, the following terms have the meanings ascribed to them.

"Enhance(s) growth" or "enhancing growth" refers to promoting, increasing or improving the rate of growth of the plant or increasing or promoting an increase in the size of the plant.

"Plant" refers to any life form that synthesizes cellulose including higher plants characterized by roots, stems and foliage and lower plants and plant-like organisms such as cryptophytes, yeasts, fungi, molds, cyanobacteria and algae.

"Ketoester" refers to compounds of keto-ester chemical structure and are natural products that confer attractive flavors and fragrances to plants such as those in the rose family and the pineapple family. Common ketoesters include α-ketoesters and β-ketoesters; and preferred ketoesters, named herein without exclusion of others of the numerous ketoesters, include such as for example the following:

Acetate esters, such as,
ethyl acetate and methyl acetate;
Acetoacetate esters, such as,
Benzyl acetoacetates;
Butyl acetoacetate and derivatives, such as, iso-butyl acetoacetate;
Dodecyl acetoacetate
Methyl acetoacetate (MAA);
Ethyl acetoacetae (EAA) and derivatives, such as, for example, ethyl 2-ethyl acetoacetate, ethyl-2-isopropyl acetoacetate, ethyl-cycloacetoacetylglycoside;
Heptyl acetoacetate;
Hexyl acetoacetate, and derivatives, such as, cyclohexylacetoacetate, and Z-3-hexen-1-yl acetoacetate;
Phenyl acetoacetates;
Propropyl acetoacetate, and derivatives, such as isopropyl acetoacetate;
Butanoate esters, such as,
ethyl 3-oxo-2-(phenylmethyl)butanoate;
salts; derivatives;
and the like.

Numerous ketoesters are additives to foods, fragrances, and perfumes, including many of the above and the following additional examples:
amyl acetoacetate;
iso-amyl acetoacetate;
para-anisyl acetoacetate;
bergamot acetoacetate;
cinnamyl acetoacetate
geranyl acetoacetate
jasmin acetoacetate
laevo-menthyl acetoacetate The most highly preferred β-ketoester is EAA because it is sparingly soluble in water, Generally Regarded As Safe (GRAS), available in bulk tonnage quantities at relatively low cost, and pleasantly fragrant.

Metal-ketoesters include preferred nutritive metal-ketoester-coordination complexes that are wholly accessible nutrients, for example, copper-, iron-, manganese-, potassium-, and zinc-ketoesters; such as, copper-MAA, copper-EAA, iron-EAA, sodium-EAA, manganese-EAA, potassium ethyl acetate; potassium-EAA; and zinc-EAA. These compounds may advantageously release their nutrients into plant metabolism. The metal-EAA is bidentate, and thus, does not have the stability of cyclic and higher polydentate chelates. Therefore, formulation is incompatible with cyclic, penta- or sexidentate chelates, for example ED3A or EDTA, because these and other polydentate (tridentate, and higher) chelates are of higher binding orders. Polymeric plastic bottles are susceptible to leakage of ketoesters, therefore, storage and shipment in glass or sheet metal containers is recommended. In particular, polystyrene bottles will dissolve in EAA, and to maintain integrity of containers, it is advisable to avoid general polymeric plastics for storage of compositions of ketoesters.

"Micellar NanoParticle" (MNP) is a nanoscopic particle making up a multiphasic emulsion. When a metal is at the core of a coordination complex of a single MNP, it may be referred herein as a metal-MNP and may be selected to facilitate transmembrane transporters, preferably of the monocarboxylate transporter (MCT) family. For correction of deficiencies in soils, blends of trace metals may be formulated as "metal-MNPs" hereinafter referred to by the trademark, μPlex™. The example of FIG. 2 presents a schematic diagram of methods and compositions for an MNP as follows: A metal-ketoester is dissolved in a compatible ketoester; the composition is mixed into aqueous solution at the Critical Micelle Concentration of the ketoester; and, therefore, resulting in the MNP.

"Glycoside" refers to any of the glycosides and derivatives, e.g., glycoside with alkyl, acyl, aryl, ketoester, polyacyl, and polyalkyl substitutions; aryl-, acyl-, and alkylpolyglycoside; aldose and ketose, preferably, pentose, hexose, heptose, and the like; and combinations thereof. Glycosides may include methylglucoside, methylmannoside, mannose; glucose; indoxylglycoside; gluconic; gluconolactone; galactose; lactose; cycloketoesterglycoside; polyalkylglycoside, for example, tetraacetyl-α-D-glycoside; derivatives, and the like. Glycosides require formulation with the specific divalent cations, calcium and manganese.

"Percent" or "%" is percent by weight unless otherwise indicated.

"Ppm" refers to parts per million by weight.

"Aqueous" refers to solutions or solvents that consist primarily of water, normally greater than 80 weight percent water and can be essentially pure water in certain circumstances. For example, an aqueous solution or solvent can be distilled water, tap water or the like. However, an aqueous solution or solvent can include water having substances such as pH buffers, pH adjusters, organic and inorganic salts, ketones, alcohols (e.g. MeOH, EtOH, and the like), sugars, amino acids or surfactants incorporated therein. The aqueous solution or solvent may also be a mixture of water and minor amounts of one or more cosolvents that are miscible therewith. Agronomically suitable organic solvents include, for example, alcohols, acetone, and ketoesters. The embodiments are incompatible with exogenous non-polar solvents such as fats, oils, and hexanes because of preferential transfers into a non-polar solvent. However, clear benefits are derived by the preferential tendency to transfer to endogenous non-polar compounds such as by deposit of micellar cargo into the waxy cuticle of a leaf. Transport of nutrients to endogenous systems that are slowly metabolized permit nutritional benefits over the long duration.

In certain embodiments the ketoester and sources of carbon (C) employed in methods and compositions of the embodiments disclosed herein preferably also comprise soluble nutrients, such as a source of nitrogen (N) and other fertilizers in at least the level the embodiments of the methods and compositions. A surfactant may be added, in particular to foliar formulations. The combination of sources of C with N is especially important for safe treatments and for growth of plants. The preferred ammoniacal nitrogen source is provided at between 200 to 2000 ppm. The ketoesters employed preferably comprise a full complement of plant nutrients as known by the art.

The pure ketoester compound, EAA, is a viscous liquid at room temperature and it is often advantageous to provide it in concentrated liquid form, such as by dispersing, solubilizing, or otherwise admixing EAA as a metal-MNP for application The amount of MNP in the carrier will depend upon the particular cosolvent that is selected and the method of application. A preferred cosolvent is an alcohol and butanol is most highly preferred because it decreases the CMC. On the other hand, a metal ketoester, when soluble in lower $C_1$ to $C_3$ alcohols, affords a degree of hydration with a small amount of, for example, isopropanol, between 0.01% to 10% of the volume of ketoester. Thus, the EAA compound may be presolubilized in a water-soluble alcohol carrier, such as propanol and/or butanol, by adding the compound minimally to 0.1-9% concentrations, and allowing the compound to quickly dissolve. Thereafter, it is made convenient for the grower to stir the final solution containing the ketoester and cosolvent formulation into water as the carrier of choice for final dilution. In most instances, the application of stirring, agitation, or even heat facilitates the dissolution of the safened ketoester product in the carrier. In the final solution of ketoester, the cosolvent component is applied at between 0.088% to 9% concentration, preferably between 0.3% to 3%, and most preferably the cosolvent is of equiMolar concentration to the ketoester; whilst the formula is safened by incorporation of 1000-1500 ppm available N and 50-250 ppm available P.

In certain embodiments the resulting mixture may be applied to all parts of the plant including the leaves, shoots, roots, stems, flowers and fruits depending on whether a dry, liquid or foliar formulation is utilized.

In certain embodiments the compositions may be applied to virtually any variety of plants, fruits or organisms that photosynthesize sugars. In particular, the compositions and may be preferably applied to "higher plants" and "lower plants." Higher plants include, but are not limited to, all species having true stems, roots, and leaves. Plants which may benefit include but are not limited to all crop plants, such as, alfalfa, anise, back ciao, barley, basil, beet, blueberry, breadfruit, broccoli, brussels sprouts, cabbage, carrot, cassava, cauliflower, celery, cereals, chard, cilantro, coffee, corn, cotton, cranberry, cucumber, dill, eggplant, fennel, grape, grain, garlic, kale, leek, legume, lettuce, melon, millet, mint, mustard, oat, onion, parsley, parsnip, pea, peanut, pepper, peppermint, potato, pumpkin, radish, rice, saffron, sesame, sorghum, soy, spinach, squash, stevia, strawberry, sunflower, sweet potato, sugar beet, sugar cane, tea, tobacco, tomato, turnip, wheat, yam, zucchini and the like; pomes and other fruit-bearing plants, such as, almond, apple, avocado, banana, breadfruit, cherry, citrus, cocoa, fig, guava, macadamia, mango, mangosteen, nopales, nut, olive, papaya, passion fruit, pear, pepper, plum, peach and the like; floral plants, such as achillea, adenium, agave, ageratum, aloe, alyssum, anemone, aquilegia, aster, azalea, begonia, bird-of-paradise, bleeding heart, borage, bromeliad, bougainvillea, buddlea, cactus, calendula, camellia, campanula, carex, carnation, celosia, chrysanthemum, clematis, cleome, coleus, cosmos, crocus, croton, cyclamen, dahlia, daffodil, daisy, day lily, delphinium, dianthus, dietes, digitalis, dusty miller, euonymus, forget-me-not, fremontia, fuchsia, gardenia, gazania, geranium, gerbera, gesneriad, gladiolus, hibiscus, hydrangea, impatiens, jasmine, lily, lilac, lisianthus, lobelia, marigold, mesembryanthemum, mimulus, myosotis, narcissus, New Guinea Impatiens, nymphaea, oenothera, oleander, orchid, oxalis, pansy, penstemon, peony, petunia, poinsettia, polemonium, polygonum, poppy, portulaca, primula, ranunculus, rhododendron, rose, salvia, senecio, shooting star, snapdragon, solanum, solidago, stock, ti, torenia, tulip, verbena, vinca, viola, violet, yucca, zinnia, and the like; indoor garden and houseplants, such as African violet, Chinese evergreen, succulents, dieffenbachia, dracaena, ficus, hosta, peace lily, philodendron, pothos, rubber tree, sansevieria, chlorophytum, and the like; trees, such as Abies, birch, cedar, Cornus, cycad, cypress, Dawn Redwood, elm, ficus, fir, ginkgo, juniper, legume, magnolia, mahogany, maple, oak, palm, Picea, Pinus, Pittosporum, Plantago, poplar, redwood, saguaro, Salix, sycamore, Taxus, teak, willow, yew, sources of lumber, Christmas tree and the like; grasses, such as turf, sod, blue grass, bent grass, creeping bents, bermuda, festuca, paspalum, pennisetum, phalaris, poa, calamogrostis, elymus, helictotrichon, imperata, molina, carex, miscanthus, panicum, blends of grass seeds, and the like; and $C_3$, $C_4$, CAM plants; dwarfs; grafts; cuttings; and hybrids; and the like. Herbicical formulations may be enhanced by supplementation with ketoester formulations and methods of the embodiments for herbicidal treatment of nuisance plants such as, for example, weeds, broadleaf weeds, grass weeds, poison oak, poison ivy, brush, chaparral, understory, and nutsedge.

The formulations and methods of the embodiments disclosed herein are generally applicable to all higher plants and protistans, to further include, but are not necessarily limited to the following: plant and algal sources of biofuels, such as switchgrass, jatropha, euphorbia, botryococcus, macrocystis, diatom, cyanobacteria, dunaliella, nannochloropsis, chlorella, haematococcus, and the like; lichen; algae, such as kelp, Eucheuma, laver, nori, kombu, wakame, Chlorophyta, Rhodophyta, Phaeophyta, and dinoflagellate; moss; liverwort; and fern. This list is intended to be exemplary and is not intended to be exclusive. Other photosynthetic organisms which may benefit by application of the compositions and methods of the present embodiments will be readily determined by those skilled in the art.

In certain embodiments the methods and formulations disclosed herein may be used to enhance growth in juvenile and mature plants, as well as cuttings and seeds and micropropagation. Thus, seed priming prior to plantings and seed coatings may be applied. Generally, the plant location to which the composition of the method is applied should have a surface area large enough to enable the plant to absorb the composition. For example, it is desirable that the plants include the sprouted cotyledon (i.e., the "seed leaves") or other substantial surfaces that facilitate absorption, such as the true leaves. Fruit bearing plants may be treated before and after the onset of bud, fruit and seed formation. For plants such as annuals, perennials, trees, orchids, gesneriads, and cacti in which the stems, roots and/or trunks may be photosynthetic, application methods include treatment of shoots with foliar sprays and/or treatment of shoots and roots by sprench application or by separate root and shoot applications.

In accordance with certain embodiments, treating plants and enhancing plant growth may be achieved by applying one or more ketoesters to a photosynthetic organism in the form of a coordination complex supplemented with one or more glycosides, in between the range of 0.001-10%, or hydrates thereof or ester derivatives thereof, or salts thereof. The solutions of coordination complexes and glycosides may be applied separately, serially, simultaneously, and preferably within the same tank mix, exemplified by a µPlex™ MNP. Suitable glycosides for use in the methods and compositions of the present invention include the acyl, alkyl, and aryl glycosides, hexoses, as well as any of a wide variety of glycoside derivatives, other biologically or chemically equivalent substances, and any combination of the foregoing. Suitable substituted glycosides include, but are not limited to compounds such as α-glycosides and combinations thereof. Any of the foregoing glycosides may be combined for use in the methods and compositions of the embodiments disclosed. Currently, the preferred glycosides for use in the methods and compositions of the present invention include alkyl-, acyl-, and aryl-α-D-glycosides, and combinations, thereof. Examples of glycosides include the following: methylglycoside; methylpolyglycoside; α-D-glucose; α-D-mannose; xylose; arabinose; polyalkylglycoside; polyacylglycoside such as tetraacetylglucoside; electron-donating arylglycoside such as para-aminophenyl-α-D-mannopyranoside; indoxylglycoside; and the like. In the case of a preferred substituted ketoester, emulsification with a ketoester solvent in the form of a µPlex™ may be an option for cellular delivery.

Where the tank mix is made, the symporter characteristics of metal chelated ketoester are appropriate to enhance the activity of pesticides and herbicides.

The formulations employed may be applied to the plants using conventional application techniques. Plants, whether juvenile or mature, may be treated at any time before and during seed development. Fruit bearing plants may be treated before or after the onset of bud or fruit formation. Improved growth occurs as a result of the exogenous application of safened ketoester formulated with other appropriate nutrients and additives.

In certain embodiments the formulations employed may also include any of a wide variety of agronomically suitable additives, adjuvants, or other ingredients and components that can improve or at least do not hinder the beneficial effects of the safened ketoester (hereinafter "additives") to provide the compositions disclosed herein. Generally accepted additives for agricultural application are periodically listed by the United States Environmental Protection Agency. For example, foliar compositions may contain spreaders present in an amount sufficient to further promote wetting, emulsification, even distribution and penetration of the active substances. Spreaders are typically organic alkanes, alkenes or polydimethylsiloxanes that provide a sheeting action of the treatment across the phylloplane. Suitable spreaders include paraffin oils and polyalkyleneoxide polydimethylsiloxanes. Suitable surfactants include anionic, cationic, nonionic, and zwitterionic detergents; for example, amine ethoxylates, alkyl phenol ethoxylates, phosphate esters, polyalkylene oxides, polyalkylene glycols, polyoxyethylene (POE) fatty acid esters, POE fatty diglycerides, POE polymers, POP polymers, PEG polymers, sorbitan fatty acid esters, alcohol ethoxylates, sorbitan fatty acid ester ethoxylates, ethoxylated alkylamines, quaternary amines, sorbitan ethoxylate esters, substituted polysaccharides, alkyl polyglucosides, block copolymers, random copolymers, polyalkylsiloxanes, polysiloxanes, tallow amines, and blends. Surfactant preference is for POE/POP polymers, trisiloxanes, alkyl polyglucosides, and alkoxylate-fatty acids. Available commercial surfactants include PELRIG, PLURONIC, TEEPOL, BRIJ, IGEPOL, TWEEN, TRITON, AGRI-DEX, TWEEN, tallow amine, detergent and the like. Commercial siloxane spreaders include PELSIL, DOW CORNING, SILWET, DYNE-AMIC, FREEWAY, SIL ENERGY, KINETIC, and the like. Alkyl polyglycosides include TRITON CG, GLUCOPON ARGIL PG, AG6202, CLASS ACT, and the like. Penetrants include, for example, sodium dodecylsulfate, formamides and alcohols. The preferred surfactants are block copolymers, and most highly preferred are POE-POP-POE, typically indicated at 0.1% in aqueous solution with characterized surface tensions. At CMC, ketoesters synergistically reduce the amount of surfactants, and vice versa, thus, providing a benefit of cost savings. For example, in the presence of CMC EAA, the effective formulation of a representative POE-POP-POP block copolymer is reduced from 0.1% down to 0.05-0.02% effective final concentration in the foliar compositions of the invention. When ketoesters such as MAA, EAA and/or propyl acetoacetate (PAA) are applied at or above respective CMCs and are transported into cells, they benefit growth of green plants through carbon input to the path of carbon in photosynthesis.

In addition to the foregoing additives, the formulations may also advantageously include one or more conventional fertilizers. Suitable fertilizers for inclusion in the formulations, methods and systems of the embodiments disclosed herein will be readily determinable by those skilled in the art and include sources of plant nutrients containing elements such as nitrogen, phosphorus, potassium, sulfur, calcium, magnesium, iron, manganese, zinc, copper, boron, molybdenum, cobalt, chlorine, carbon, silicon, hydrogen, oxygen, and the like. Compounds with a combination of major nutrients are currently preferred, particularly ammonium phosphates and potassium phosphates and salts and derivatives thereof. In particular, in cases requiring foliar-N, ammoniacal-, urea-, hexamine-, and nitrate-nitrogen fertilizers are most preferred. In order to support rapid vegetative growth, the most highly preferred fertilizers for inclusion in ketoester formulations are, especially ammonium salts, low biuret urea and nitrate salts, preferably ammonium sulfate, ammonium phosphates, urea, potassium nitrate, and calcium nitrate, within the supplemental nitrogen content range of 0.1% to 46%. For example, 0.9% ketoesters may be formulated with the nitrogen sources that combine two elemental requirements each, such as, 0.1% to 10% ammonium sulfate and 0.01% to 5% ammonium phosphates. Variations in the compositions may be made for enhancement of flowering and pigmentation by adjusting the N—P—K ratios, for instance, reduction of N and enhancement of P by adding potassium phosphates to a source of N in a manner that they intensify flowering and fruiting. Fertilizer supplementations such as these may be made by addition to the tank mix or they may be undertaken as separate applications or in simultaneous applications.

The amount of fertilizer added to the formulations will depend upon the plants to be treated, nutrient content, irrigation, or deficiencies of the media. Generally, fertilizers may be present in amounts sufficient to balance growth attained with ketoesters when applied to the plant. Typically, the conventional fertilizers are included as blends in the amount of between about 200 ppm and about 5000 ppm by weight of the foliar composition. High potency is achieved by shoot or root application of formulations which provide the ketoester in combination with conventional plant nutrients at rates of application generally known by the art, thereto.

In addition to ketoesters and cosolvents as provisions of fixed carbon input to crops, the formulations may also include any of various secondary nutrients, such as sources of sulfur, calcium, and magnesium; as well as sources of essential micronutrient elements, B, Cl, Co, Cu, Fe, Mn, Mo, Na, Ni, Si, Zn, and the like, which are formulated in a manner consistent with conventions of the art. For example, sources of these nutrients include the following: primary fertilizers, as salts and/or mixes; secondary fertilizers, as salts or mixes; and micronutrients, preferably as salts or mixes of salts. Formulations including N—P—K with chelated micronutrient supplementations are applicable in tank mixes; and, in pH 5 to pH 6 foliar formulations, micronutrient salts, may be formulated. For example, sulfate, nitrate, and chloride salts; salicylates, such as potassium-, cupric-, and zinc-salicylates; oleates, such as cupric oleate and manganese oleate; citrates; and acetates, such as, Mn acetate, Zn acetate, Co acetate, Mg acetate, and hydrates, and the like. Other constituents which may be added to the compositions include manures, microbials, soil conditioners, pesticides, fungicides, antibiotics, plant growth regulators, GMO, gene therapies and the like. Among the plant growth regulators which may be added to the formulations of the present invention are auxins; brassinolides; cytokinins; gibberellins; amino acids; benzoates; vitamins; carbohydrates; herbicides, such as, phosphonomethylglycine; sulfonylurea; halosulfuron alkyl; salts, esters, phosphates, hydrates and derivatives thereof; and genetic compositions.

Exogenous ketoesters may be applied to plants with N-safeners during the day or night. Without being necessarily bound by a particular theory, metabolism is energetically consumptive of sources of phosphates comprising a safener. For example, acetoacetate Coenzyme A ligase involves ATP to ADP. The metabolism of a ketoester is related to the nanostructure, alcohol dehydrogenase, with inferred alcohol. In different pathways, metabolism of ketoesters to their organic components may result in direct acceptors of electrons in PSI and PSII. Furthermore, acetoacetates play roles in transmembrane transport, for example, the proton-linked MCT family catalyzes the transport of acetoacetate for rapid movement across the plasma membrane into cells, and as a first step of treatment, penetrates. In other pathways, the formulation of a ketoester with a compatible glycoside in the presence of manganese and calcium, may provide conditions for intracellular displacement of hexoses and oligosaccharides. The nanotechnology is appropriate for application in the dark, as during periods of the respiratory metabolism of plants. Ketoesters will degrade in alkaline environments, therefore, it is highly recommended to maintain formulations in between pH 5.0 to 6.8 and preferably at between pH 5.5 to 6.5 mildly acidic solution.

In general, in certain embodiments the methods disclosed herein comprise the steps of producing a formulation that is readily miscible in water and applying the resulting MNP directly to the plants and/or the rooting medium; furthermore, direct blending of a µPlex™ composition in water is provided. In certain embodiments the concentration of ketoester in the formulations should generally be between about 0.1 to 80% and more preferably between about 0.9 to 2.5%. For specific applications, the concentration of ketoester should be lower for roots than for shoots; thus, between 0.1% to 1% for root application; and for foliage, between the concentrations equal to or greater than the CMC, yet less than the highest concentration for solubility in water, approximately between 25 to 35 parts water. When diluted in an aqueous carrier, the resulting diluted mixture of CMC ketoester and one or more metabolizable compounds, preferably glycoside, is applied to a photosynthetic organism in an amount of about 3 to 100 gallons/acre wherein the preferred concentration of a glycoside is between about 0.001% and 10%. Foliar application devices must be continuously agitated throughout the period of application to maintain suspension of MNPs. Agitation in crop sprayers or tractors with spray booms is achieved by cycling solutions through the supply tanks with continuously integrated pumping mechanisms. Based on metabolic pathways, ketoesters and their coordination complexes may contribute to enhanced photosynthesis and, by reducing the energetic loss of photorespiration, are suggested in a safened system; as for example, as an adjunct to cultivation of plants in the presence of saturated light intensities, such as by sunlight refraction by glass microbeads, the pre-treatment of plants with the following exemplary formulations of safened ketoester complexes is recommended. Glass microbeads may be sodalime silicate or borosilicate, preferably sodalime; 10-2000 microns diameter, preferably 600-800 microns diameter, and blends thereof; 1.2-1.9 refractive index (RI), preferably 1.3-1.7 RI, and most preferably 1.5 RI; and distributed beneath a leaf in a layer from 0.5 mm to 1 m depth, preferably 1 mm depth and preferably contiguous when applied to enhance ambient light intensity.

The following examples are provided to illustrate the methods disclosed herein and should not be construed as limiting. In these examples, purified water was obtained through reverse osmosis; EAA was obtained from GFS; Versene® Ag Mn and Versonal® Ag Fe were obtained from Dow Chemical; and PelLok 9591 random block copolymer surfactant was obtained from Pelron. Abbreviations used in the following examples are defined as follows: "RBC" means a random block copolymer surfactant such as PelLok 9591; "Q2 5211 SuperWetter" means Dow Corning Q2 5211 Superwetter Polysiloxane; "EAA" means ethyl acetoacetate; "Fe(III)-EAA" means ferric(III)-ethyl acetoacetate; "Cu(II)-EAA" means cuprous(II)-ethyl acetoacetate; "IPA" means isopropanol; "α-MeG" means methyl-α-D-glucoside; $(NH_4)_2SO_4$ means ammonium sulfate; "MKP" means monopotassium phosphate; "DKP" means dipotassium phosphate; "MAP" means monoammonium phosphate; "DAP" means diammonium phosphate; "MNP" means micellar nanoparticle; "L" means liter; "ml" means milliliter; "mg" means milligram; "g" means gram; "Kg" means kilogram; "mM" means milliMolar; "ppm" means parts per million; and "Micronutrients" means soluble trace metals, for example, in the ranges and preferred ppm of EXAMPLE 2.

MAP, DAP, MKP and DKP are utilized as interchangeable nutrient sources and buffers, adjustable to desired pH of the solution. Foliar solutions were formulated at pH 6.

The following are examples of specific formulations that may advantageously be employed in methods to treat plants and to enhance growth in plants. The following examples are intended to provide guidance to those skilled in the art and do not represent an exhaustive list of formulations within the scope of the embodiments disclosed.

Example 1

Conditioner

| Component | Range g/L | Preferred g/L |
|---|---|---|
| EAA | 8.6 to 28 | 8.6 |
| Micronutrients | 0.1 to 10X | 1X |
| MAP | 1 to 50 | 8 |

Dissolve the ketoester component in the order given. Dissolve MAP into 1 L of water with stirring. Finally, add ketoesters with stirring and agitate rapidly until dissolved. Dissolution of the EAA requires thorough mixing over time, approximately 0.5 to 24 hours, to dissolve at room temperature, 25 to 35° C.; however, if the ambient water temperature is below that required, pre-solubilize the ketoesters with 9% volume of butanol. For example, if the water temperature is 20-25° C., and the total weight of EAA+micronutrients=9 g/L, then admixture of 8 g/L n-butanol is recommended.

Apply 10 to 100 gallons/acre as close to the roots as possible. With irrigation, water the treatment into the soil, toward the roots. Besides its action as a nutrient safener, MAP will provide a mildly acidic solution. For treatments of roots that are not in alkaline support media, there exists an option to adjust the pH of the formulation with a buffer, such as by adding DKP to bring the pH to a higher value. The addition of DKP to the EAA+MAP formulation will have the added benefit of providing all three major fertilizer components, NPK.

Example 2

Foliar Formulation

| Ingredient | Range g/L | Preferred g/L |
|---|---|---|
| αMeM | 0.001-0.1 | 0.005-0.1 |
| LB Urea | 0.6-3 | 1 |
| Ca(NO$_3$)$_2$ | 0.1-5 | 1 |
| Mg(NO$_3$)$_2$ | 0.1-5 | 1 |
| RBC | 0.3-1 | 0.5 |
| EAA | 8-30 | 9 |

| Micronutrients | Range ppm | |
|---|---|---|
| Mn | 0.5-18 | 6 |
| Cu | 0.2-1.2 | 0.5 |
| Zn | 0.2-1.5 | 0.2 |
| B | 0.2-2 | 0.2 |
| Mo | 0.001-0.01 | 0.002 |
| Fe | 1-20 | 3 |

Dissolve the nutrients in 1 Liter of water; adjust to a range between pH 5 to pH 6 with gluconic, citric, salicylic, mineral acid, or buffer; and add micronutrients with stirring. Add EAA and RBC into formula with stirring into the aqueous solution. Apply to foliage at spray to glisten volume, approximating 75 gallons/acre.

As an exemplary treatment of plants with this formulation, initially, twenty plants were matched in diameter and maintained in one-gallon plastic containers each, separated into equal populations of Treated and Controls. Applications were applied to shoots of the Treated population of 10 cacti in spray to glisten volume. Controls were also sprayed to glisten, but with the same nutrients without EAA, IPA, or glycoside. In all other ways, Control and Treated populations were cultivated side-by-side under identical field conditions. After 16 weeks, the diameters of the plants beneath spines were measured. The results showed that the nutrient controls averaged 10 cm mean diameter and the treated population averaged 12.5 cm mean diameter; statistically significant within 95% confidence interval; $p=0.01$; $n=10$. Representative samples from nutrient Control (left) and Treated (right) populations of Golden Barrel Cactus (*Echinocactus grusonii*) are exhibited in FIG. 3.

Example 3

Two Components Convenience Formulation: 1, 2 Punch Micronutrients are from Example 2

| Component 1 Ingredient | Preferred g/L | Upper Range g/L |
|---|---|---|
| $(NH_4)_2SO_4$ | 0.3 | 1 |
| MKP | 0.20 | 0.6 |
| DKP | 0.17 | 0.5 |
| α-MeM | 0.005 | 1.0 |
| $Ca(NO_3)_2$ | 0.1 | 2 |
| Micronutrients | 1X | 0.1-5 X |

| Component 2 | | |
|---|---|---|
| Low Biuret Urea | 0.6 | 9 |
| EAA | 1 | 80 |
| IPA | 0.3 | 800 |
| RBC | 0.3 | 1 |

| 1, 2 Punch |
|---|
| Make up each of the two components as concentrates comprising a kit for which the dry and liquid components may be stored, diluted, and applied separately; or the components may be mixed and applied together. |
| For admixture, add Component 1 into 1 L of water with stirring and after it is completely dissolved, add Component 2 into the same 1 L solution with stirring. |
| After the two components are mixed together, they are applied as a foliar spray to shoots of plants at 10 to 100 gallons/acre. |

Example 4

| Fe-MNP Ingredient | g/L |
|---|---|
| 70% IPA | 1 |
| Hexamine | 1 |

-continued

| Fe-MNP Ingredient | g/L |
|---|---|
| EAA | 10 |
| Fe(III)-EAA | 0.01 |
| Surfactant | 1 |

In the exemplary preferred formulation of an Fe-MNP of Example 4, make up the above solution and, immediately prior to foliar application, completely dissolve into 1 Liter water or as a tank mix with stirring into a compatible agrichemical. Finally, adjust to between pH 5.5-6.5 by buffering with MKP and DKP. Apply the Fe-MNP foliar spray to glisten.

Example 5

| MNP Formula Ingredient | g/L | Range g/L |
|---|---|---|
| Fe(III)-EAA | 0.001 | 0.10 |
| Cu(II)-EAA | 0.001 | 0.10 |
| n-Butanol | 0.1 | 800 |
| EAA | 9 | 27 |
| LB Urea | 1.2 | 6 |

Stir Fe(III)-EAA and Cu(II)-EAA into butanol until they are completely dissolved. Dissolve urea into the solution. Stir EAA into the alcoholic solution until dissolved. Thoroughly mix solutions with each addition. This concentrate may be scaled up proportionally and stored. For field utilization, bring the volume up to 1 liter with water with thorough agitation. Adjust to pH 5.5 with MKP/DKP phosphate buffer, as needed. Transfer the MNP formulation into an agitated misting device and apply to foliage for copper and iron supplementation, preferably in the range of 10 to 75 gallons/acre. The concentration of iron in 1 L is preferably approximately 3 ppm, and the solution may be adjusted between 0.5 ppm to 15 ppm iron, as needed for correction of deficiency by delivery by means of this Cu-MNP and Fe-MNP.

Example 6

Zn-MNP, Range in Grams/Liter (g/L)

| Ingredient | g/L |
|---|---|
| $(NH_4)_2SO_4$ | 1.3-3.9 |
| MKP | 0.02-2 |
| Urea | 0.6-3 |
| IPA | 0.1-1 |
| EAA | 8-30 |
| Zinc-EAA | 0.003-0.3 |

Dissolve zinc-EAA in isopropanol and mix with EAA. Dissolve remaining components into 1 Liter water; adjust to pH 5.5 to pH 6.5 with MKP; and add with stirring into the aqueous solution to make Zn-MNP. Apply to rooting medium at 10 to 100 gallons/acre and water in to root zone with irrigation.

Example 7

Glycoside Formulation, Range in Grams/Liter (g/L)

| Ingredient | g/L |
|---|---|
| $(NH_4)NO_3$ | 1.3-4.5 |
| MKP | 0.02-2 |
| Micronutrients | 1-2X |
| α-Mannoside | 0.002-2 |
| Q2 5211 SuperWetter | 0.1-0.5 |

Mix all components in 1 liter of water with rapid agitation until completely dissolved; and adjust to between pH 5 to pH 7 with MKP. Apply to foliage at 3-100 gallons/acre for enhancement of $C_7$ in a plant. This glycoside component may be blended with an appropriate ketoester, such as 1-30 g/L MAA, EAA, and/or PAA.

Example 8

Exemplary Nutrient Blend, Percent Values

| Component | Range | Preferred |
|---|---|---|
| Polyacetyl glycopyranose | 0.1-100 | 1 |
| Gluconate | 0.001-10 | 0.02 |
| Water | 5-80 | 53 |
| Urea | 1-60 | 11 |
| EAA | 0.1-25 | 5.8 |
| Fe-EAA | 0.01-1 | 0.1 |
| Mn-EAA | 0.01-1 | 0.1 |
| $Ca(NO_3)_2$ | 0.1-30 | 3 |
| Pluronic L92 | 0.001-10 | 1 |
| Butanol | 0.1-100 | 0.6 |

Example 9

Separated Dry and Liquid Compositions for Mixing Together into a Single Aqueous Foliar Formulation

| Dry Ingredient | Range g/L | Preferred g/L |
|---|---|---|
| $(NH_4)NO_3$ | 0.1-10 | 0.3 |
| MKP | 0.2-2 | 0.8 |
| DKP | 0.1-1.5 | 0.3 |
| α-MeG | 1-200 | 6 |
| $Ca(NO_3)_2$ | 0.01-10 | 5 |
| $Mn(NO_3)_2$ | 0.001-0.05 | 0.002 |

| Liquid | | |
|---|---|---|
| Low Biuret Urea | 0.3-0.9 | 0.6 |
| EAA | 8.6-30 | 9 |
| $Fe(NO_3)_3$ | 0.001-0.01 | 0.04 |
| Pluronic L92 | 0.05-5 | 0.1 |
| IPA | 0.1-5 | 0.8 |

Mixing Directions

Make up each of the dry and liquid compositions as concentrates without water, the paired dry and liquid comprising a kit for which they may be stored separately in concentrated form. Thereafter, they may be mixed into water and applied together. For admixture, add the dry crystals into 0.5 L of water with stirring and after completely dissolved, add the liquid solution into the aqueous solution with rapid agitation, such as stirring. Bring the total volume to 1 L with the addition of water.

After the two components are mixed together, they are applied as a foliar spray to shoots of plants at 10 to 100 gallons/acre.

Example 10

μPlex™ Foliar Concentrate

| Ingredient, by order of addition | % Weight of formula |
|---|---|
| EAA | 30.0 |
| $Fe(NO_3)_3$ | 0.4 |
| IPA | 0.9 |
| Pluronic L92 | 2.2 |
| Water | 44 |
| Low Biuret Urea | 10.9 |
| $Mn(NO_3)_2$ | 0.2 |
| $Ca(NO_3)_2$ | 4.1 |
| $Mg(NO_3)_2$ | 3.1 |
| α-MeM | 3.6 |
| MKP | 0.2 |
| DKP | 0.1 |
| Zn-salicylate | 0.3 |

Make 5 gallons of the above μPlex™ concentrate by adding each compound in order of addition with agitation. Make the organic solvent solution separately from the water solution. IPA may be substituted with butanol. The two may be stored separately or they may be added together and stored as a biphasic solution. Finally, adjust to pH 5.5 with DKP and MKP, as needed.

For field utilization, dilute the entire 5 gallons of concentrate in 100-500 gallons of water, mix thoroughly for an hour or more, and apply to 5 acres of crops as a foliar spray, mist, or fog. Where nutrient deficiencies are indicated, additional supplementation may be formulated, for example, by addition of potassium salicylate, cupric salicylate, and/or cupric chloride.

Example 11

Exemplary Advantage® System with µPlex™ Concentrate Formulation and with Glass Microbeads for Enhancement of Light Intensity

| Ingredient, by order of addition | % Weight of formula |
|---|---|
| MAA | 20.0 |
| $Fe(NNO_3)_3$ | 0.5 |
| n-Butanol | 2.0 |
| Pluronic L62 | 1.0 |
| Water | 57.0 |
| Urea | 10.8 |
| $Mn(NO_3)_2$ | 0.2 |
| $Ca(NO_3)_2$ | 4.1 |

| Ingredient, by order of addition | % Weight of formula |
|---|---|
| MKP | 0.3 |
| α-MeM | 0.5 |
| DKP | 0.1 |

Make the ketoester solution separately from the water solution. Make 5 gallons of the above concentrate by adding each compound in order of addition with agitation until dissolved. Finally, adjust to pH 5.5 with DKP/MKP, as needed. For greenhouse utilization, dilute the entire 5 gallons of concentrate into 100-500 gallons of water, stir thoroughly for 1 hour, and apply to shoots as a foliar spray/mist/fog/sprench over 5 acres. Following the foliar application, and after the surface of the foliage has dried, evenly spread 700 micron diameter glass microbeads below the plants and on top of the ground surface to make a 1-5 mm thick refractive layer. Gluconate/glucoheptanate may be substituted for MKP for pH-adjustment.

Example 12

Fe-MNP

A process for novel synthesis of an MNP from iron salt is as follows: The aqueous saturated solution of 1 g ferric chloride hexahydrate is dissolved in 10 ml EAA with rapid stirring for 1 minute or more to the formation of the coordination complex. Solution is allowed to sit without agitation for 8 hours or until the solution shows biphasic layers. The Fe-EAA fraction may be decanted or collected by separatory funnel. Notably, Fe-EAA, is insoluble in water, but soluble in IPA. The Fe-EAA may be dissolved into equal or lesser volumes of IPA or alcohols mixture; and then into compatible 9 g ketoesters with stirring, such as MAA, and/or EAA, yielding the μPlex™ product. For μPlex™ to MNP, mix μPlex™ into 1 L water with rapid stirring, yielding Fe-MNP in between the range of 1 to 25 ppm Fe. This novel Fe-MNP is micellar EAA-Fe-EAA and is a plant micronutrient supplement for correction of deficiencies of iron. Similarly, zinc-EAA and copper-EAA may be solubilized in aqueous solution to zinc-MNP and copper-MNP supplements, or combinations, thereof.

The following is an exemplary range of effective foliar application dose based on safened ketoester formulations and the results show synergism using the EAA formulations of the safened invention as compared to each of EAA and Cosolvent controls.

Plant Type EAA (mM) Cosolvent (mM) EAA+Cosolvent (mM)

Petunia 100 9000 65+5

Experimental biology investigations show an exemplary synergism of EAA to random block copolymer (RBC) using the formulations of the invention to visually determine the effect of concentration of the compounds on the effective spreading of water droplets on waxy foliar surfaces of oleander leaves. The following is an exemplary effective spreading of water droplet on a waxy leaf based on EAA synergist:

Leaf Plant Type Effective water droplet spreading

RBC EAA RBC+EAA

Oleander 0.6% 1% 0.3%+0.86%

Example 13

| μPlex ™ Concentrate for Tank Mix | |
|---|---|
| Ingredient, by order of addition | % Weight of formula |
| EAA | 30 |
| Butanol | 3 |
| Water | 30 |
| Ammonium sulfate | 13 |
| $Mn(NO_3)_2$ | 1 |
| $Ca(NO_3)_2$ | 5 |
| α-MeG | 17 |
| pH 5.5 Buffer | 1 |

Make 5 gallons of the above μPlex™ concentrate by adding each compound in order of addition with agitation. Make the organic solvent solution separately from the water solution. The two may be stored separately or they may be added together and stored as a biphasic solution. Hexamine, urea, or nitrate may be utilized as nitrogen sources where appropriate. Finally, adjust to pH 5.5 with a buffer such as phosphate, gluconate, and/or organic acid, as needed.

For field utilization, dilute the entire 5 gallons of concentrate in 100-800 gallons of water, make the tank mix with appropriate pesticide, biostimulant, antagonist, synergist, systemic, bioagent, additive, effector, genetic, surfactant, and/or the like, thoroughly for an hour or more, and apply to 1-20 acres of crops as a foliar spray, mist, or fog.

Although specific features of the invention are described with respect to one example and not others, this is for convenience only as some feature of one described example may be combined with one or more of the other examples in accordance with the methods and formulations disclosed herein.

What is claimed is:

1. A method of enhancing the growth of a photosynthetic organism, comprising applying to said organism an effective amount of a formulation comprising a micellar metal chelated ketoester, wherein said formulation comprises an aqueous solution of said metal chelated ketoester in an amount of at least 20% by weight, and a solvent for said metal chelated ketoester.

2. The method of claim 1, wherein said metal in said metal chelated ketoester is selected from the group consisting of zinc, copper, iron, manganese, calcium, cobalt, magnesium and potassium.

3. The method of claim 1, wherein said ketoester is an alkyl acetoacetate.

4. The method of claim 1, wherein said ketoester is selected from the group consisting of methyl acetoacetate, ethyl acetoacetate and propyl acetoacetate.

5. The method of claim 1, wherein said formulation further comprises a glycoside.

6. The method of claim 1, wherein said solvent comprises the same ketoester that is present in said metal chelated ketoester.

7. The method of claim 1, wherein said solvent is an aliphatic alcohol.

8. The method of claim 1, wherein said solvent is butanol.

9. The method of claim 1, wherein said formulation further comprises a safening agent selected from nitrogen and phosphorous.

10. The method of claim 1, wherein said metal chelated ketoester is in the form of micellar nanoparticles.

11. The method of claim 1, wherein said photosynthetic organism is a plant.

12. The method of claim 1, wherein said photosynthetic organism is in the presence of glass microbeads.

13. A micellar composition comprising an aqueous solution of a metal chelated ketoester at or above its critical micelle concentration, and a solvent for said metal chelated ketoester.

14. The micellar composition of claim 13, wherein said metal chelated ketoester is in the form of nanoparticles.

15. The micellar composition of claim 13, wherein said solvent is an aliphatic alcohol.

16. The micellar composition of claim 13, further comprising a glycoside.

17. The method of claim 1, wherein said photosynthetic organism is a seed.

18. A method of enhancing facilitation of the transport into a plant of an active agent comprising applying a formulation comprising an aqueous solution of a micellar metal chelated ketoester in an amount of at least 20% by weight, and a solvent for said metal chelated ketoester to said plant in combination with said active agent.

19. The method of claim 18 wherein said active agent comprises a pesticide.

\* \* \* \* \*

UNITED STATES PATENT AND TRADEMARK OFFICE
CERTIFICATE OF CORRECTION

PATENT NO.         : 9,828,299 B2                                    Page 1 of 1
APPLICATION NO.    : 14/397718
DATED              : November 28, 2017
INVENTOR(S)        : Arthur M. Nonomura It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 89 days.

Signed and Sealed this

Twenty-fifth Day of September, 2018

Andrei Iancu
*Director of the United States Patent and Trademark Office*